United States Patent
Suzuki et al.

(10) Patent No.: US 12,396,650 B2
(45) Date of Patent: Aug. 26, 2025

(54) SUBDURAL SENSOR

(71) Applicant: ANT5 Co., Ltd., Yamaguchi (JP)

(72) Inventors: Michiyasu Suzuki, Yamaguchi (JP);
Sadahiro Nomura, Yamaguchi (JP);
Takao Inoue, Yamaguchi (JP);
Toshitaka Yamakawa, Kumamoto (JP)

(73) Assignee: ANT5 Co., Ltd., Yamaguchi (JP)

( * ) Notice: Subject to any disclaimer, the term of this patent is extended or adjusted under 35 U.S.C. 154(b) by 474 days.

(21) Appl. No.: 18/086,390

(22) Filed: Dec. 21, 2022

(65) Prior Publication Data

US 2023/0129638 A1 Apr. 27, 2023

Related U.S. Application Data

(63) Continuation of application No. PCT/JP2021/024617, filed on Jun. 29, 2021.

(30) Foreign Application Priority Data

Jun. 29, 2020 (JP) .................................. 2020-112158

(51) Int. Cl.
*A61B 5/03* (2006.01)
*A61B 5/00* (2006.01)
*G01L 9/00* (2006.01)

(52) U.S. Cl.
CPC ............ *A61B 5/031* (2013.01); *A61B 5/6864* (2013.01); *G01L 9/0026* (2013.01)

(58) Field of Classification Search
None
See application file for complete search history.

(56) References Cited

U.S. PATENT DOCUMENTS

| | | | |
|---|---|---|---|
| 7,120,481 | B2 | 10/2006 | Keller et al. |
| 2004/0039270 | A1 | 2/2004 | Keller et al. |

(Continued)

FOREIGN PATENT DOCUMENTS

| | | | |
|---|---|---|---|
| JP | 2004-504092 A | 2/2004 | |
| JP | 2011-83315 A | 4/2011 | |

(Continued)

OTHER PUBLICATIONS

International Search Report issued in PCT/JP2021/024617 mailed on Sep. 21, 2021 with English Translation (5 pages).

(Continued)

*Primary Examiner* — Duane N Taylor, Jr.
(74) *Attorney, Agent, or Firm* — Nakanishi IP Associates, LLC

(57) ABSTRACT

A subdural sensor includes: a substrate formed of a flexible material; and at least one type of sensor part mounted on the substrate. The substrate has an elongated shape, and includes: a sensor area in which the sensor part is mounted and a wiring pattern connected to the sensor part is formed; a wiring area contiguous with the sensor area, the wiring pattern extending in the wiring area; and a connector area contiguous with the wiring area, the connector area being an area on which a connector to be connected to the wiring pattern extending from the wiring area is mounted. A tip part of the sensor area has a planar shape that curves convexly toward an outer periphery, and a side shape that curves toward a first surface, the first surface being on the side of a dura mater when the subdural sensor is inserted into the subdural space.

18 Claims, 19 Drawing Sheets

(56) References Cited

U.S. PATENT DOCUMENTS

| | | | |
|---|---|---|---|
| 2010/0179518 A1* | 7/2010 | Ludvig | A61B 5/6882 |
| | | | 604/891.1 |
| 2015/0038948 A1* | 2/2015 | Ludvig | A61B 5/375 |
| | | | 604/891.1 |
| 2017/0035316 A1 | 2/2017 | Kuzniecky et al. | |
| 2021/0267523 A1* | 9/2021 | Donoghue | A61N 1/0529 |

FOREIGN PATENT DOCUMENTS

| | | |
|---|---|---|
| JP | 2015-221177 A | 12/2015 |
| JP | 6296606 B2 | 3/2018 |
| WO | 02/07592 A1 | 1/2002 |

OTHER PUBLICATIONS

Written Opinion of International Searching Authority issued in PCT/JP2021/024617 mailed on Sep. 21, 2021 with English Translation (8 pages).

Toshitaka Yamakawa, et al., "Implantable Multi-Modality Probe for Subdural Simultaneous Measurement of Electrophysiology, Hemodynamics, and Temperature Distribution", IEEE Transactions on Biomedical Engineering, vol. 66, No. 11, Nov. 2019, pp. 3204-3211 (8 pages).

\* cited by examiner

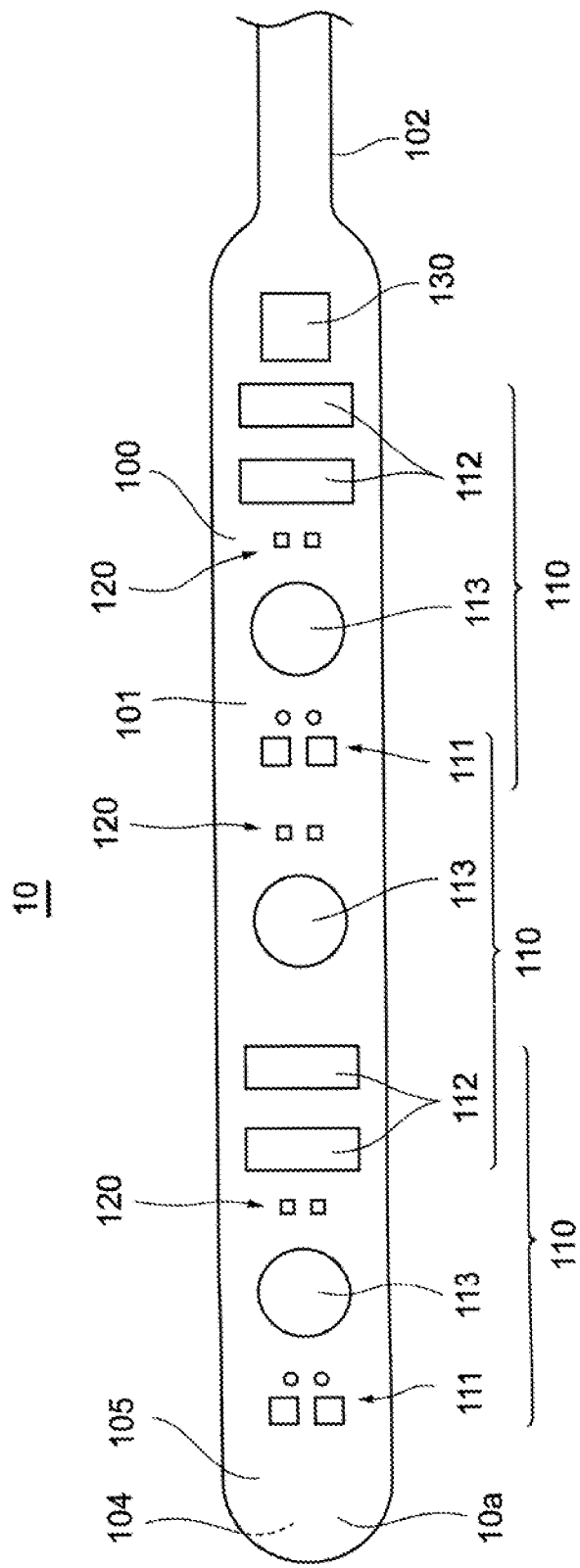

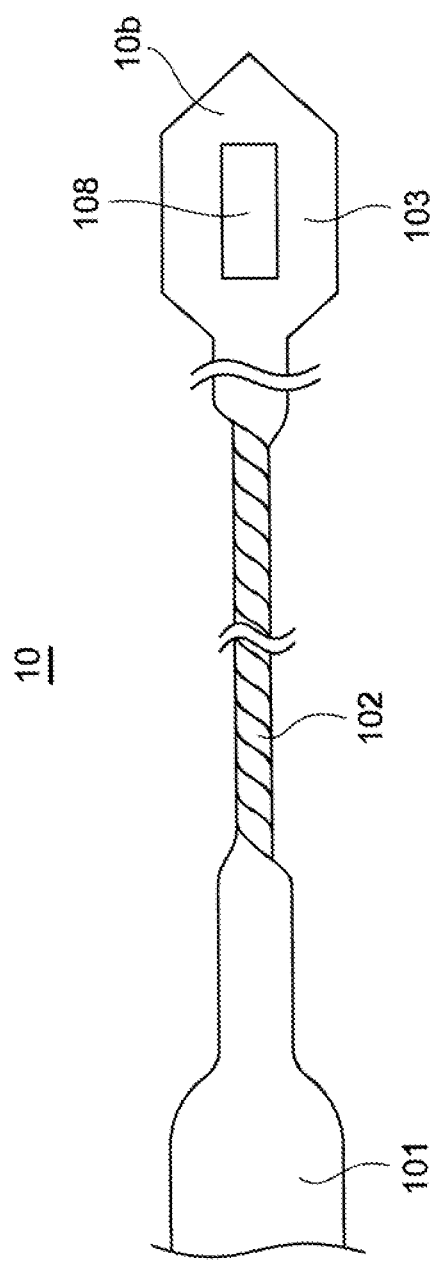

SUBDURAL SENSOR

CROSS-REFERENCE TO RELATED APPLICATION(S)

This application is a continuation application of PCT International Application No. PCT/JP2021/024617 filed on Jun. 29, 2021, which designated the United States, and which claims the benefit of priority from Japanese Patent Application No. 2020-112158, filed on Jun. 29, 2020. The entire contents of these applications are incorporated herein by reference.

BACKGROUND OF THE INVENTION

Field of the Invention

The present invention relates to subdural sensors for acquiring biological information by being arranged in a subdural space.

Description of the Related Art

In the treatment of patients with brain disease or brain injury, in addition to identifying the symptoms themselves, such as increase in intracranial pressure (ICP), epilepsy, and reduction in cerebral blood flow, it is important to accurately monitor brain pathological conditions ahead of the appearance of such symptoms and/or the occurrence of severe events in order to identify risks more quickly.

Regarding the acquisition of biological information of the brain, for example, JP6296606 B and Toshitaka Yamakawa, et al., "Implantable Multi-Modality Probe for Subdural Simultaneous Measurement of Electrophysiology, Hemodynamics, and Temperature Distribution", IEEE Transactions on Biomedical Engineering, Vol. 66, No. 11, November 2019, pp. 3204-3211, disclose subdural sensors that make contact with or are inserted into the subdural space and measure hemodynamics at least close to the brain surface. The subdural sensors disclosed in JP6296606 B and Yamakawa, et al. can simultaneously measure cerebral blood flow, brain tissue oxygen saturation (brain StO2), electroencephalogram, and brain temperature.

Edema or hematoma resulting from cerebral infarction or trauma may result in increased intracranial pressure (ICP), which may cause brain hypoxia or neuronal death due to the reduction of cerebral blood flow. Decompressive craniotomy may be performed to reduce ICP. Another serious sequela is elevation of brain temperature causing neuronal death. In order to suppress this temperature elevation, cerebral hypothermia therapy is established, which cools the brain to a therapeutic temperature level predetermined. As an example, JP2011-083315 A discloses a system for regionally cooling the brain. Although the cerebral protective effect by general hypothermia by which the whole body is cooled, little is known about focal brain cooling. Therefore, sufficient brain information obtained from this sensor is quite important in order to exert cerebral protective effects by the focal cooling.

BRIEF SUMMARY OF THE INVENTION

A subdural sensor, which is one aspect of the present invention, is to be arranged in a subdural space and acquires biological information about the brain. The subdural sensor comprises: a substrate formed of a flexible material; and at least one type of sensor part mounted on the substrate, wherein the substrate has an elongated shape as a whole, wherein the substrate includes: a sensor area in which the at least one type of sensor part is mounted and a wiring pattern connected to the at least one type of sensor part is formed; a wiring area contiguous with the sensor area on one end thereof, the wiring pattern extending in the wiring area; and a connector area contiguous with the other end of the wiring area, the connector area being an area on which a connector to be connected to the wiring pattern extending from the wiring area is mounted, and a tip part of the sensor area has a planar shape that curves convexly toward an outer periphery, and a side shape that curves toward a first surface, the first surface being on the side of a dura mater when the subdural sensor is inserted into the subdural space.

The above-described and other features, advantages and technical and industrial significance of the present invention, will be better understood by reading the following detailed description of the current preferred embodiments of the present invention while considering the attached drawings.

BRIEF DESCRIPTION OF THE DRAWINGS

FIG. 1A is a plan view schematically showing a portion of a subdural sensor according to one embodiment of the present invention.

FIG. 2 is a plan view schematically showing a portion of a subdural sensor according to one embodiment of the present invention.

DETAILED DESCRIPTION OF THE INVENTION

Hereinafter, a subdural sensor according to embodiments of the present invention will be described with reference to the drawings. It should be noted that the present invention is not limited by these embodiments. In the description of each drawing, the same parts are denoted by the same reference numbers.

The drawings referred to in the following description are merely schematic representations of shape, size, and positional relationship to the extent that the subject matter of the present invention may be understood. In other words, the present invention is not limited only to the shapes, sizes, and positional relationships illustrated in the respective figures. In addition, the drawings may also include, among themselves, parts having different dimensional relationships and ratios from each other.

Embodiments of Subdural Sensor

Figure 1B:
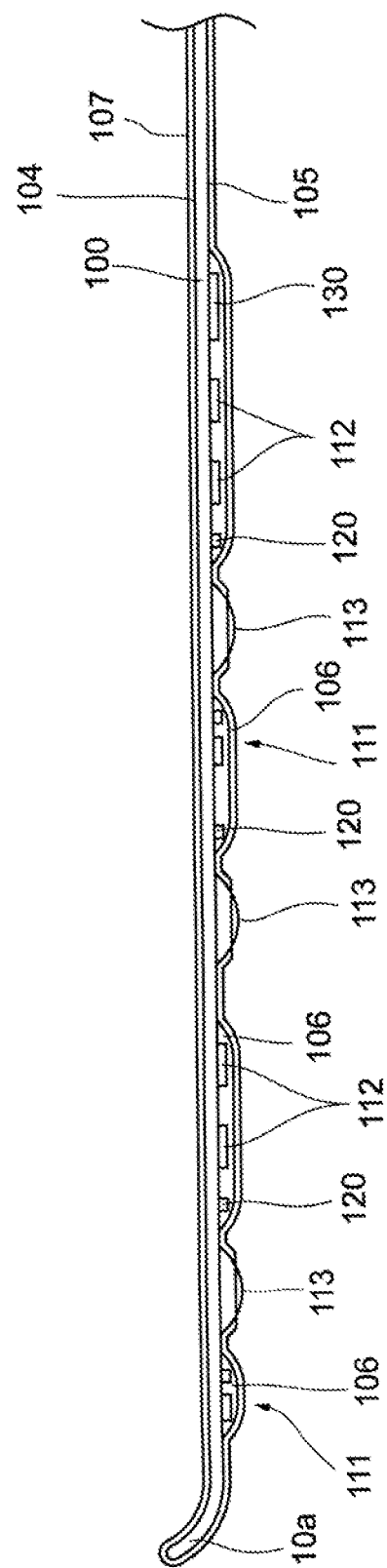
FIG. 1B is a side view schematically showing the portion of the subdural sensor according to one embodiment of the present invention.

FIG. 1A is a plan view schematically showing a portion of a subdural sensor according to one embodiment of the present invention. FIG. 1B is a side view schematically showing the portion of the same subdural sensor. FIG. 2 is a plan view schematically showing another portion of the same subdural sensor. The subdural sensor 10 according to the present embodiment is a device arranged in the subdural space and acquires biological information about the brain. The sensor is equipped with a substrate 100 formed of a flexible material and at least one type of sensor part mounted on the substrate 100.

The substrate 100 is a so-called flexible substrate that is flexible and is formed of resin materials, such as polyimide. The substrate 100 and the sensor parts are coated in an integral manner with biocompatible materials such as Parylene (registered trademark), except for the vicinity of the apex of a light reflection part 113, which will be described later. The thickness of the film 107 is not particularly limited, but in the case of using, for example, Parylene (registered trademark), the thickness may preferably be set to, for example, 5 μm to 20 μm, in order to prevent significant loss of the flexibility of the substrate 100.

As shown in FIGS. 1A to 2, the substrate 100 has a generally elongate shape, and includes a sensor area 101 in which at least one type of sensor part is arranged, a wiring area 102 that is continuous with the base end of the sensor area 101 on one end thereof, and a connector area 103 that is continuous with the other end of the wiring area 102. These sensor area 101, wiring area 102, and connector area 103 are preferably formed in an integral manner by a single flexible substrate. In the sensor area 101, the wiring area 102, and the connector area 103, a wiring pattern connected to the sensor parts is continuously formed. The wiring pattern may be formed only on one surface or on both surfaces. Alternatively, it may be formed over several layers.

The sensor area 101 is an area inserted into the subdural space, where the sensor parts are mounted and the wiring pattern connected to the sensor parts is formed. Here, the sensor area 101 is inserted in the subdural space so that the surface (first surface) 104 is on the side of the dura mater and the back (second surface) 105 is on the side of the brain surface. FIG. 1A shows a plurality of sensor parts arranged in a line along the longitudinal direction on the back 105 of the sensor area 101.

Preferably, the tip part 10a of the sensor area 101 has a planar shape that curves convexly toward the outer periphery, as shown in FIG. 1A. In addition, the tip part 10a preferably has a side shape that curves toward the surface 104, as shown in FIG. 1B.

A portion of the wiring area 102 on the side of the sensor area 101 is placed in vivo together with the sensor area 101. On the other hand, a portion of the wiring area 102 on the side of the connector area 103 is arranged in vitro together with the connector area 103. The wiring area 102 and the sensor area 101 are preferably connected at an obtuse angle or in a gentle curve in order to prevent disconnection of the substrate 100. The same applies to the connection portion between the wiring area 102 and the connector area 103.

The wiring pattern formed in the sensor area 101 extends into the wiring area 102. The wiring pattern includes a signal line for transmitting signals output from the sensor parts mounted on the sensor area 101, and a power line for supplying power to the sensor parts.

In FIG. 2, at least a portion of the wiring area 102 is wound in a coiled form so as to form a cylindrical outer periphery shape as a whole. As such, when the subdural sensor 10 is placed in vivo, the scalp can be easily and safely sutured around the wound portion using common suture techniques such as a purse-string suture. The wound portion may be coated with biocompatible materials, such as Parylene (registered trademark), silicone rubber, and the like. This makes it easier to maintain the wound shape.

The connector area 103 is mounted with a connector 108 for connecting the subdural sensor 10 to external devices such as a control device. The connector 108 is connected to the wiring pattern extending from the wiring area 102, transmits the signals output from the sensor parts mounted on the sensor area 101 to the external devices, and supplies the power from the external devices to the sensor parts. The connector 108 may be a wired connector (e.g., a male substrate-to-substrate connector) or a wireless connector. From the viewpoint of hygiene, a terminal part 10b of the connector area 103 may preferably have a planar shape that tapers toward the end thereof so that it can be pulled outward from the inside of the scalp.

Next, the sensor parts mounted on the sensor area 101 will be described. A blood flow measurement part using the principle of near-infrared spectroscopy (NIRS), a temperature measurement element (thermistor), an electrocorticogram (EcoG) measurement electrode, an intracranial pressure sensor, an acceleration sensor, a Doppler blood flow meter, or the like, may be mounted as the sensor part. FIGS. 1A and 1B show a plurality of blood flow measurement parts 110, a plurality of temperature measurement elements 120, and an intracranial pressure sensor 130, as examples of the sensor parts. As described later, an electrocorticogram measurement electrode 114 (see FIG. 3) is arranged at the bottom of the light reflection part 113 of the blood flow measurement part 110. These sensor parts are mounted on the back 105 of the substrate 100.

It is preferable if biological information, such as cerebral blood flow, brain temperature, and electroencephalogram, can be acquired simultaneously at multiple locations in the brain. Therefore, in the present embodiment, three channels of each of the blood flow measurement part 110, the temperature measurement element 120, and the electrode 114 are provided. The number of channels of these sensor parts is not particularly limited, and the length of the sensor area 101 may be increased accordingly in order to increase the number of channels.

Each sensor part, except for the light reflection part 113, may preferably be coated with an insulation part 106 made of materials with biocompatibility and high light transparency, such as silicone rubber (e.g., polydimethylsiloxane (PDMS)). The insulation part 106 is placed in a round shape so as to wrap around the edges of each sensor part. The film 107 covers the entire surface of the substrate 100 and these insulation parts 106.

The blood flow measurement part 110 includes a light-emitting element 111 capable of emitting near-infrared light, a light-receiving element 112 capable of receiving the near-infrared light, and a light reflection part 113 arranged between the light-emitting element 111 and the light-receiving element 112. The light-emitting element 111 emits near-infrared light into the brain. The light-receiving element 112 receives the near-infrared light reflected in the brain, and converts this near-infrared light signal into an electrical signal and outputs the same.

Figure 3:
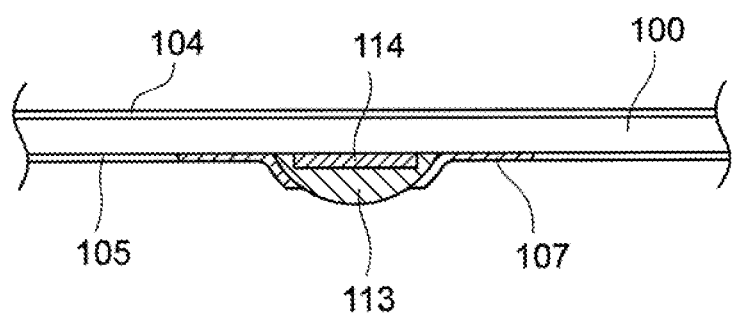
FIG. 3 is a partial cross-sectional view showing the vicinity of a light reflection part shown in FIG. 1A.

FIG. 3 is a partial cross-sectional view showing the vicinity of the light reflection part 113. The light reflection part 113 is formed of a metal with biocompatibility and good conductivity, such as platinum (Pt). The film 107 is formed such that, while it covers the boundary between the light reflection part 113 and the substrate 100, the apex of the light reflection part 113 is exposed.

As shown in FIG. 3, the light reflection part 113 has a shape in which the circumferential part thereof bulges toward the inner periphery. Since the surface of the light reflection part 113 comes into contact with the brain surface, it is preferable for the light reflection part 113 to have a shape without edges, such as a dome shape.

The light reflection part 113 reflects the near-infrared light again, which is emitted from the light-emitting element 111 and reflected in the brain, in the direction into the brain. As a result, the near-infrared light escaping to the outside of the brain may be reduced and the near-infrared light reflected in the brain may be allowed to enter the light-receiving element 112 efficiently, therefore, the sensitivity for the gray matter portion located in relatively shallow regions within the brain can be improved. In addition, the light reflection part 113 reflects, at the circumferential part thereof, the near-infrared light which is emitted from the light-emitting element 111 in the direction into the brain. As a result, the near-infrared light may be suppressed from directly entering the light-receiving element 112 from the light-emitting element 111, and the S/N ratio of the signal acquired in the blood flow measurement may be improved.

At the bottom of the light reflection part 113, an electrode 114 is arranged, which is mounted on the substrate 100 for electrocorticogram measurement, and the light reflection part 113 is placed so as to wrap this electrode 114. In other words, the light reflection part 113 is electrically connected to the electrode 114 and also acts as an electrode for electrocorticogram measurement. The light reflection part 113 bulges from the back 105 of the substrate 100 and is easily brought into contact with the brain surface, making it possible to improve the detection sensitivity for the cortical potential. In addition, since the solder for mounting the electrode 114 is sealed by the light reflection part 113, the electrical connection between the electrode 114 and the living body may be secured while safety to the living body is assured.

The height of the light reflection part 113 is preferably approximately 0.5 mm or more, or more preferably approximately 0.7 mm or more, in order to fully wrap the electrode 114. In addition, in order to smoothly insert the sensor area 101 under the dura mater, the height of the light reflection part 113 is preferably approximately 1 mm or less.

(Usage Example of Subdural Sensor)

Figure 4:
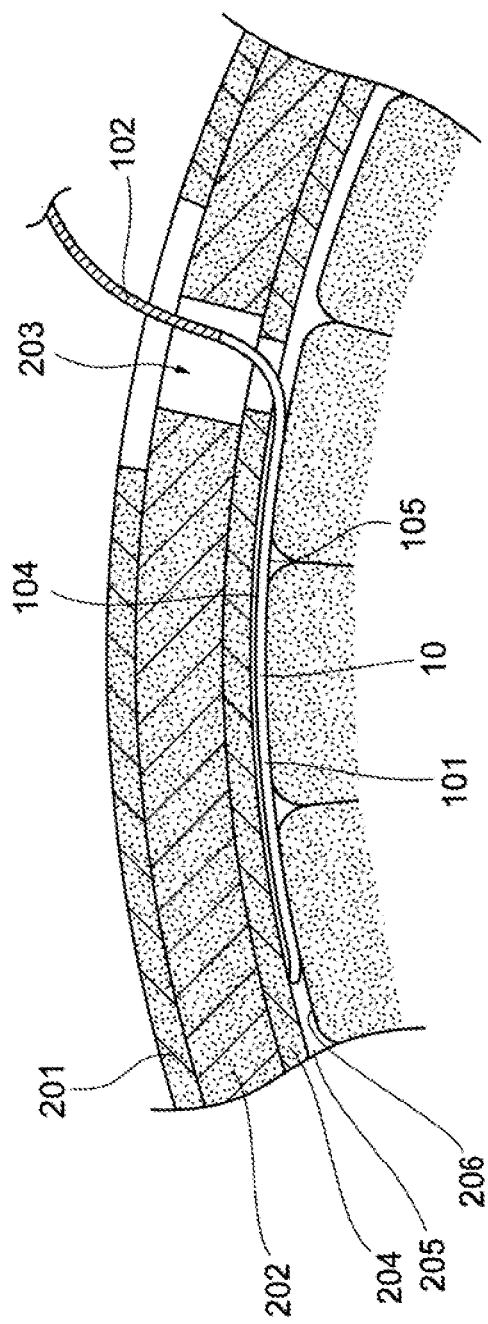
FIG. 4 is a schematic diagram showing a usage example of a subdural sensor according to one embodiment of the present invention.

FIG. 4 is a schematic diagram showing a usage example of the subdural sensor 10 according to one embodiment of the present invention. When using the subdural sensor 10, an incision is made in the scalp 201, a burr hole 203 is opened in the skull 202, and a small incision is made in the dura mater 204, from which the subdural sensor 10 is inserted into a subdural space 205 such that the surface 104 of the sensor area 101 is on the side of the dura mater 204. Then, the subdural sensor 10 is pushed forward along the brain surface 206 (over the arachnoid mater) to be arranged at a target region of the brain surface 206. On the other hand, in vitro, the connector 108 (see FIG. 2) provided in the connector area 103 is connected to a measurement system, and after checking the operation of the subdural sensor 10, the scalp 201 is sutured around the wiring area 102.

Here, there are generally two ways to place the sensor under the dura mater: placing the sensor by exposing the brain after performing a craniotomy and making an incision in the dura mater; and, as described with reference to FIG. 4, making a small incision in the dura mater from a burr hole opened in the skull and inserting the sensor via the small incision in the dura mater along the brain surface into the subdural space. Since the incision is small, the latter way is advantageous over the former from the viewpoint of infection risks and stable retention of the sensor. It can be said that the latter way is also preferable in the case where the sensor is placed in the brain for a period of time (e.g., two weeks) in order to monitor biological (brain) information.

On the other hand, when inserting the subdural sensor from the small incision in the dura mater, it is necessary to push the subdural sensor to the target region on the brain surface, and it is preferable to use materials that have flexibility, but have a certain degree of elasticity, as materials for the substrate, in order to perform the above task. Specifically, as mentioned above, a substrate may be used in which a resin material, such as polyimide, is coated with, for example, Parylene (registered trademark). However, with such subdural sensor, the operator must push the sensor forward through the subdural space such that the tip of the subdural sensor does not touch the brain surface, based on the sensation of the brain surface rather than visual confirmation. Therefore, advanced manipulation may be required for the operator in order to safely arrange the subdural sensor in the target region.

Therefore, in the subdural sensor 10 according to the present embodiment, the planar shape of the tip part 10a is curved convexly toward the outside, and the side shape of the tip part 10a is curved toward the surface 104. As a result, the subdural sensor 10 can be safely and easily inserted into the subdural space 205 via the small incision in the dura mater 204.

In detail, since the tip part 10a is curved toward the surface 104 side, the tip part 10a is unlikely to come into contact with the brain surface 206 when the subdural sensor 10 is pushed forward along the brain surface 206 in the subdural space 205. Therefore, this prevents the end of the subdural sensor 10 from touching the brain surface 206. In addition, even if there is a living tissue in the same direction as the direction of travel of the subdural sensor 10, since the subdural sensor 10 comes into contact with such living tissue at the underpart of the tip part 10a (i.e., the back 105 of the curved tip part 10a), the end thereof may still be suppressed from touching the brain surface 206. Moreover, since the planar shape of the tip part 10a is curved convexly and has no corners, the impact of the end of the sensor area 101 coming into contact with the surrounding living tissue may be mitigated.

Further advantages of the subdural sensor 10 according to the present embodiment will be described below.

In general, when a sensor is placed in vivo, the wiring is pulled out of the skull from the sensor arranged in the subdural space and then the scalp is sutured.

In this regard, in the subdural sensor 10, since at least a portion of the wiring area 102 of the substrate 100 is wound so as to form a cylindrical outer periphery shape as a whole, the scalp 201 can be safely sutured around the wound portion. The scalp 201 can also be easily sutured using versatile suture techniques such as a purse-string suture.

In addition, the S/N ratio of the signal acquired in the blood flow measurement using near-infrared light can be improved in the subdural sensor 10 according to the present embodiment.

Here, in the blood flow measurement using near-infrared light, a technique is also known, in which the near-infrared light escaping to the outside of the brain is reduced in order to improve the sensitivity for the gray matter portion by placing a reflective plate between the light-emitting element and the light-receiving element (see, for example, JP6296606 B).

In contrast, in the present embodiment, the light reflection part 113 having a shape in which the circumferential part thereof bulges toward the inner periphery (e.g., a dome shape) is provided between the light-emitting element 111 and the light-receiving element 112. As a result, the near-infrared light emitted from the light-emitting element 111 can be reflected in the direction into the brain and the near-infrared light escaping to the outside of the brain can be reduced. In addition, the light reflection part 113 allows for the near-infrared light emitted from the light-emitting element 111 to be suppressed from directly entering the light-receiving element 112. In other words, the near-infrared light that enters the light-receiving element 112 without passing through the brain can be reduced.

Accordingly, in the blood flow measurement using near-infrared light, the sensitivity for the gray matter portion can be improved and the S/N ratio of the acquired signal can also be improved.

In addition, when the light reflection part 113 is formed of platinum, safety with respect to the living body may be improved and the electrical connection between the electrode 114 and the brain surface may be reliably secured, by placing the light reflection part 113 so as to wrap the electrode 114 for electrocorticogram measurement.

Moreover, according to the present embodiment, both cerebral blood flow and electroencephalogram can be measured for a common region in the brain.

(Variation of Subdural Sensor)

Figure 5A:
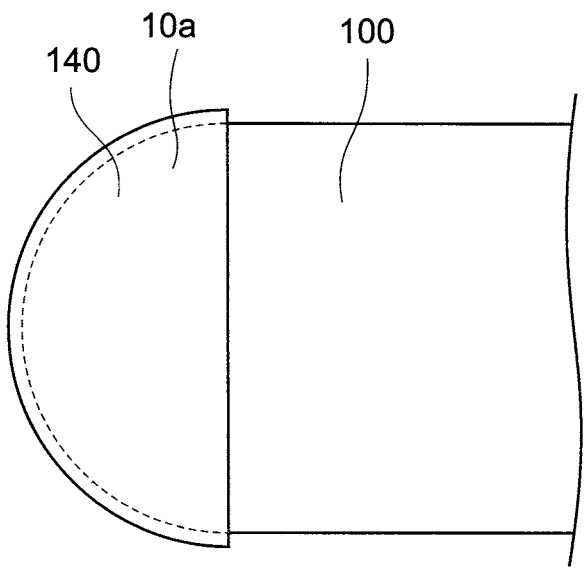
FIG. 5A is a plan view schematically showing a first variation of a tip part of a substrate.
Figure 5B:
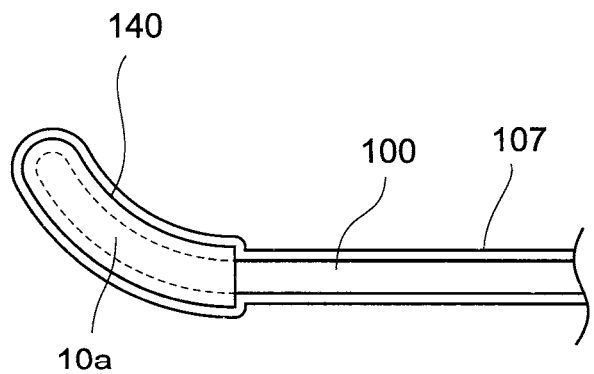
FIG. 5B is a side view schematically showing the first variation of the tip part of the substrate.

FIG. 5A is a plan view schematically showing a first variation of the tip part 10a of the substrate 100. FIG. 5B is a side view schematically showing the same variation. The subdural sensor according to the present variation further includes a cover 140 covering the tip part 10a of the substrate 100. As shown in FIG. 5B, the cover 140 and the substrate 100 may be integrally coated with the film 107, or the cover 140 may be placed on the substrate 100 coated with the film 107.

The cover 140 may preferably be formed of a flexible and biocompatible material such as silicone rubber. The cover 140 itself may have a shape that curves toward the surface 104 side. In this case, the tip part 10a of the planar substrate 100 may be deformed by placing the cover 140 on the tip part 10a. Alternatively, the cover 140 may be made to conform with the shape of the tip part 10a by placing a flexible cover 140 on the tip part 10a of the substrate 100 which is curved toward the surface 104 side.

By providing such cover 140, the end of the subdural sensor comes into contact with the living tissue in a gentle manner, further enhancing safety when inserting the subdural sensor into the subdural space. In addition, by providing the cover 140, a load is applied to the tip part 10a, so the lifting of the substrate 100 may be suppressed. As a result, various sensors may be allowed to come into close contact with the brain surface, and the accuracy of the acquired biological information may be improved.

Figure 6:
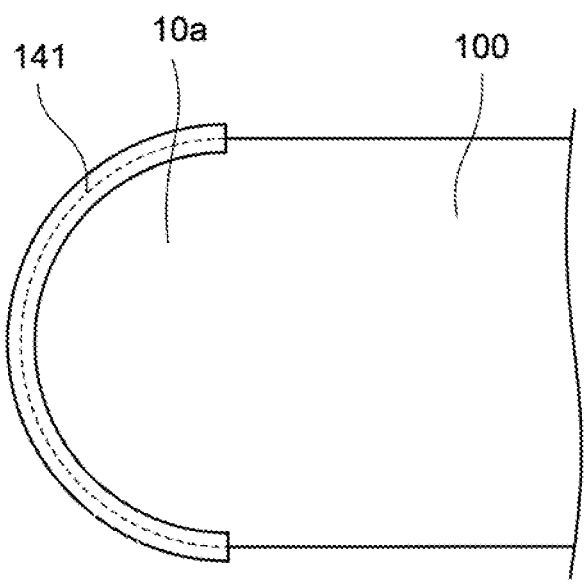
FIG. 6 is a plan view schematically showing a second variation of the tip part of the substrate.

FIG. 6 is a plan view schematically showing a second variation of the tip part 10a of the substrate 100. The side shape of the present variation is the same as FIG. 5B. As shown in FIG. 6, safety when inserting the subdural sensor into the subdural space may also be enhanced by the cover 141 covering only the end of the tip part 10a of the substrate 100.

In the case of placing a cover on the tip part of the substrate 100, the tip part may not need to be curved toward the outer periphery side. This is because the end is brought into contact with the living tissue in a gentle manner by providing a cover (although this depends on the thickness and material of the cover) and safety can be improved compared to the case without a cover.

Figure 7:
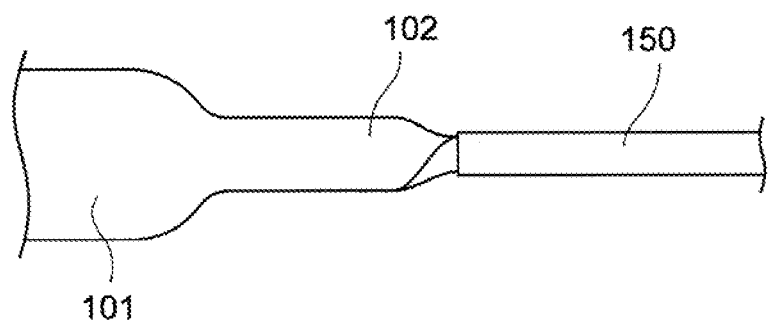
FIG. 7 is a plan view schematically showing a first variation of a wiring area of the substrate.

FIG. 7 is a plan view schematically showing a first variation of the wiring area 102 of the substrate 100. The subdural sensor according to the present variation further includes a tube 150 that accommodates therein at least a portion of the wiring area 102 of the substrate 100.

The tube 150 is formed of a flexible material such as silicone rubber. By accommodating at least a portion (specifically, a portion in the vicinity of the scalp when the subdural sensor is inserted into the subdural space) of the wiring area 102 in such tube 150, the scalp can be easily and safely sutured around the tube 150. The tube 150 can also provide the effect of protecting the wiring area 102.

Figure 8:
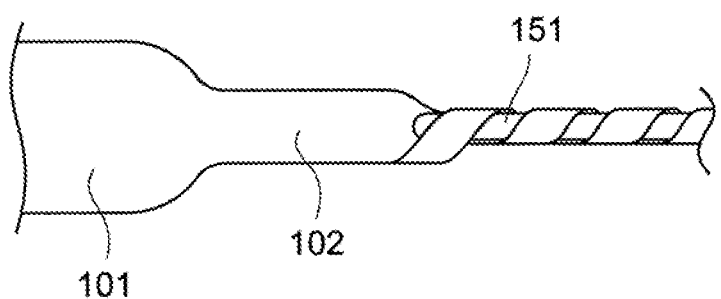
FIG. 8 is a plan view schematically showing a second variation of the wiring area of the substrate.

FIG. 8 is a plan view schematically showing a second variation of the wiring area 102 of the substrate 100. In the present variation, the wiring area 102 is wound around a core wire 151 in a coil form. The coil wire 151 is formed of a flexible material such as silicone rubber. The coil wire 151 and the wiring area 102 wound around the coil wire 151 may be coated in an integral manner with biocompatible materials, such as Parylene (registered trademark), silicone rubber, and the like. By using such core wire 151, the strength can be increased while maintaining the flexibility of the wiring area 102.

Figure 9A:
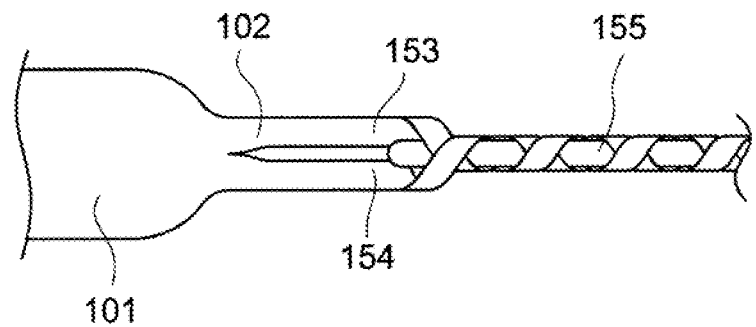
FIG. 9A is a plan view schematically showing a third variation of the wiring area (on the sensor area side) of the substrate.
Figure 9B:
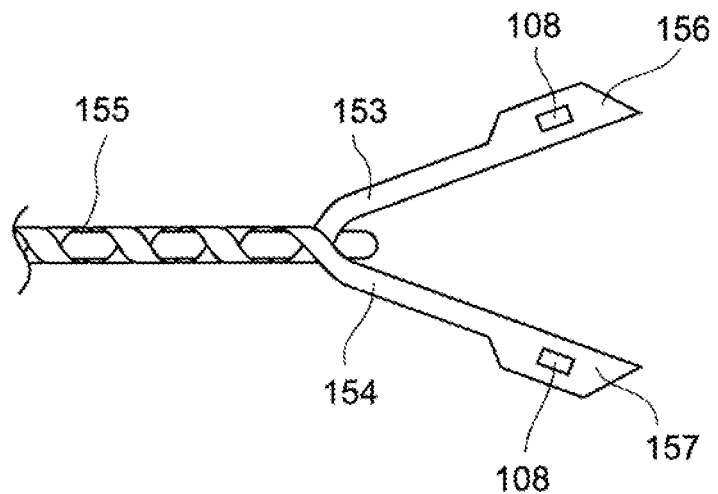
FIG. 9B is a plan view schematically showing the third variation of the wiring area (on the connector area side) of the substrate.
Figure 9C:
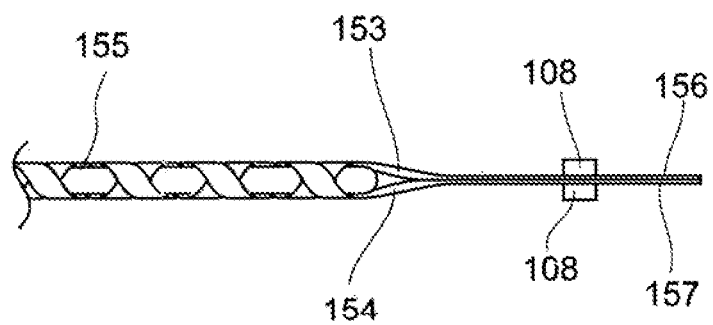
FIG. 9C is a plan view schematically showing the third variation of the wiring area (on the connector area side) of the substrate.

FIGS. 9A to 9C are plan views each schematically showing a third variation of the wiring area 102 of the substrate 100. Among which, FIG. 9A shows the sensor area side, and FIGS. 9B and 9C show the connector area side. In the present variation, at least a portion of the wiring area 102 is divided into a plurality of strip-like areas along the longitudinal direction, and each of the plurality of strip-like areas is wound around the core wire 155.

The wiring area 102 is preferably divided into an area where a signal line pattern is formed (signal area 153) and an area where a power line pattern is formed (power area 154). In this case, the signal area 153 and the power area 154 are preferably wound in opposite directions to each other, and further, they are more preferably wound so that they are orthogonal to each other. In the present variation, again, the wound signal area 153 and power area 154 may be coated with biocompatible materials, such as Parylene (registered trademark), silicone rubber, and the like.

In this way, by dividing the wiring area 102 into the signal area 153 and the power area 154 and winding them around the core wire 155, the scalp can be easily and safely sutured around the wound portion. In addition, by winding the signal area 153 and the power area 154 in opposite directions to each other, it is also possible to avoid electromagnetic noise generated in the power line being induced to the signal line and superimposed on the signal, thereby reducing the effect of noise on the signal.

In this case, a connector area 156 on the signal area 153 side and a connector area 157 on the power area 154 side may be left divided as shown in FIG. 9B, or they may be stuck together back-to-back as shown in FIG. 9C.

Figure 10A:
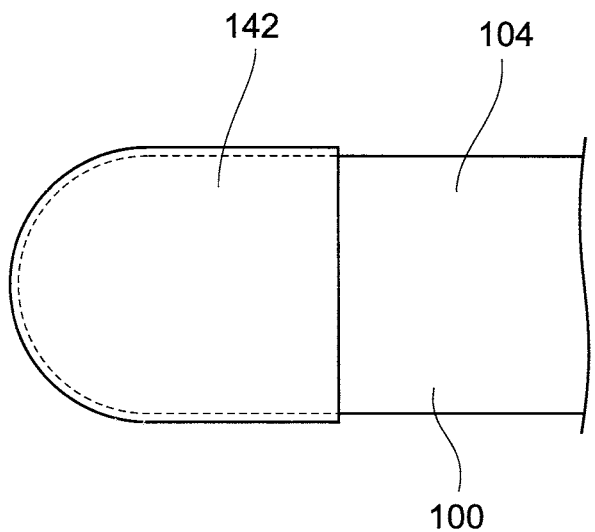
FIG. 10A is a plan view (seen from the surface) schematically showing an implementation of an intracranial pressure sensor.
Figure 10B:
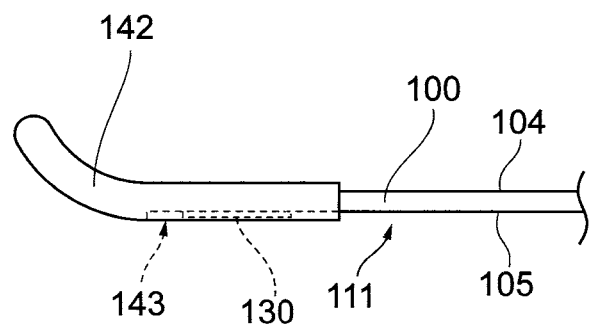
FIG. 10B is a side view schematically showing the implementation of the intracranial pressure sensor.
Figure 10C:
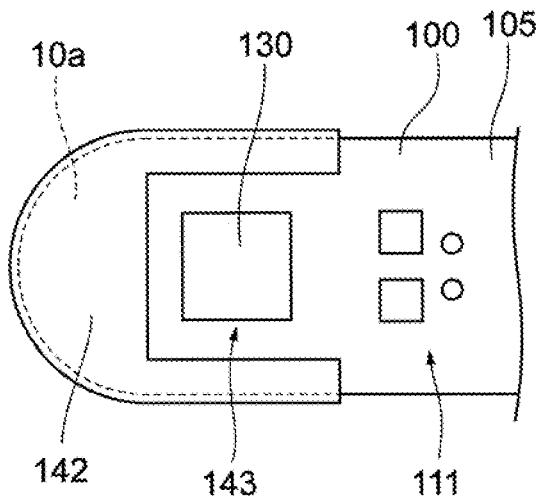
FIG. 10C is a plan view (seen from the back) schematically showing the implementation of the intracranial pressure sensor.

FIGS. 10A to 10C are diagrams each schematically showing an implementation of the intracranial pressure sensor 130. Among which, FIG. 10A is a plan view showing the surface 104 side of the substrate 100, FIG. 10B is a side view, and FIG. 10C is a plan view showing the back 105 side of the substrate 100. The intracranial pressure sensor 130 may be mounted in the vicinity of the tip part of the substrate 100, and in this case, a reinforcement cover 142 surrounding the intracranial pressure sensor 130 may preferably be provided. In addition, the reinforcement cover 142 may be coated with the film 107 integrally with the substrate 100.

As shown in FIGS. 10A and 10C, the tip part of the reinforcement cover 142 has a shape that is curved convexly toward the outer periphery side. As shown in FIG. 10B, the tip part of the reinforcement cover 142 is curved toward the surface 104 side. The reinforcement cover 142 is formed of flexible and biocompatible materials such as silicone rubber, and may have some weight in order to apply a load to the area in the vicinity of the intracranial pressure sensor 130. As shown in FIG. 10C, a U-shaped window 143 is formed on the back side of the reinforcement cover 142, and the reinforcement cover 142 is fitted onto the substrate 100 so that the intracranial pressure sensor 130 is exposed at this window 143. The intracranial pressure sensor 130 is coated with the insulation part 106, similar to the above embodiment (see FIG. 1).

According to the present variation, since the intracranial pressure sensor 130 is arranged deep in the subdural space, and the reinforcement cover 142 suppresses the lifting of the intracranial pressure sensor 130, the intracranial pressure can be measured more accurately. In addition, since the weight of the intracranial pressure sensor 130 and the reinforcement cover 142 also suppress the lifting of the substrate 100 as a whole, the accuracy of biological information acquired by other sensor parts may also be improved.

Figure 11:
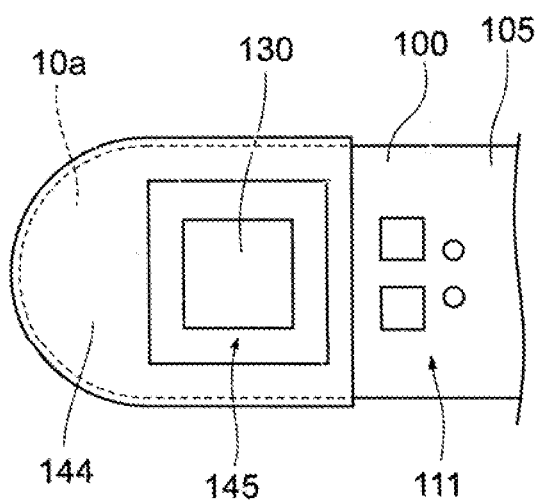
FIG. 11 is a plan view (seen from the back) schematically showing another implementation of the intracranial pressure sensor.

FIG. 11 is a plan view schematically showing another implementation of the intracranial pressure sensor 130 and showing the back 105 side of the substrate 100. On the back of the reinforcement cover 144 shown in FIG. 11, a square-shaped window 145 that exposes the intracranial pressure sensor 130 is formed. In this way, by placing the reinforcing cover 144 so as to surround the intracranial pressure sensor 130, a balanced load may be applied to the area where the intracranial pressure sensor 130 is arranged.

Figure 12:
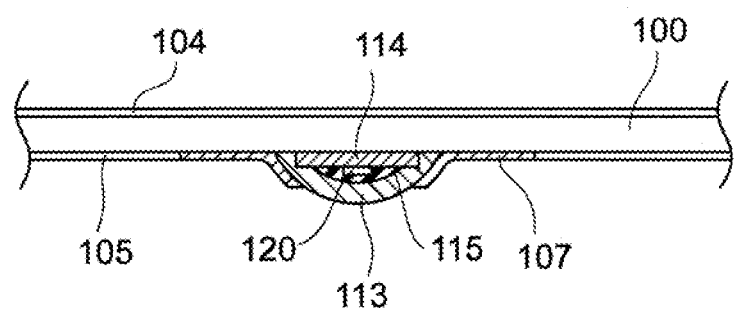
FIG. 12 is a partial cross-sectional view showing a variation of the light reflection part.

FIG. 12 is a partial cross-sectional view showing a variation of the light reflection part. In the present variation, a temperature measurement element 120 is arranged inside the dome-shaped light reflection part 113. An insulating material 115 such as polydimethylsiloxane (PDMS) is filled around the temperature measurement element 120.

By arranging the temperature measurement element 120 inside the light reflection part 113, the temperature measurement element 120 may reliably be made to come into contact with the living tissue via the light reflection part 113, and the heat conduction efficiency between the temperature measurement element 120 and the living tissue may be improved. Accordingly, the accuracy of the measurement of brain temperature may be improved. In addition, since centers of the respective regions to be measured regarding the electroencephalogram and brain temperature are aligned, cerebral blood flow, electroencephalogram, and brain temperature can be measured for a common region in the brain.

Figure 13:
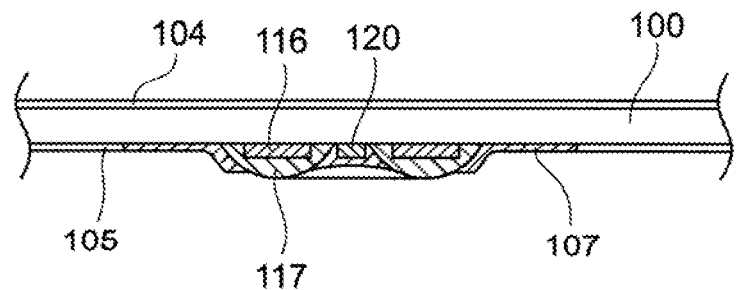
FIG. 13 is a partial cross-sectional view of another variation of the light reflection part.

FIG. 13 is a partial cross-sectional view showing another variation of the light reflection part. In the present variation, an electrode 116 for electrocorticogram detection is formed in a circular ring shape, and a light reflection part 117 is placed in a donut shape so as to wrap the electrode 116. The temperature measurement element 120 is mounted on the substrate at the center of the light reflection part 117.

As shown in FIG. 13, when at least the circumferential part of the light reflection part 117 bulges toward the inner periphery, the near-infrared light may be suppressed from directly entering from the light-emitting element 111 into the light-receiving element 112 by the circumferential part reflecting such near-infrared light. Obviously, by reflecting the near-infrared light by the entire surface of the light reflection part 117, the near-infrared light escaping to the outside of the brain may be reduced and the sensitivity for the gray matter portion may also be improved. Moreover, since centers of the respective regions to be measured regarding the electroencephalogram and brain temperature are aligned, cerebral blood flow, electroencephalogram, and brain temperature can be measured for a common region in the brain.

Further, the shape of the light reflection part may be a shape where the circumferential part bulges in a straight line toward the inner periphery, such as a truncated cone, or the portion that comes into contact with the brain surface may be planar. In any case, the shape of the light reflection part may preferably be determined so that the edges thereof are not exposed.

In the above-described embodiments and variations, the light-emitting element 111 and the light-receiving element 112 for blood flow measurement using near-infrared light are mounted on the back 105 side of the substrate 100, but the light-emitting element 111 and the light-receiving element 112 may be mounted on the surface 104 side. In this case, the substrate 100 is preferably made of a material with high light transparency with respect to at least near-infrared light.

Figure 14:
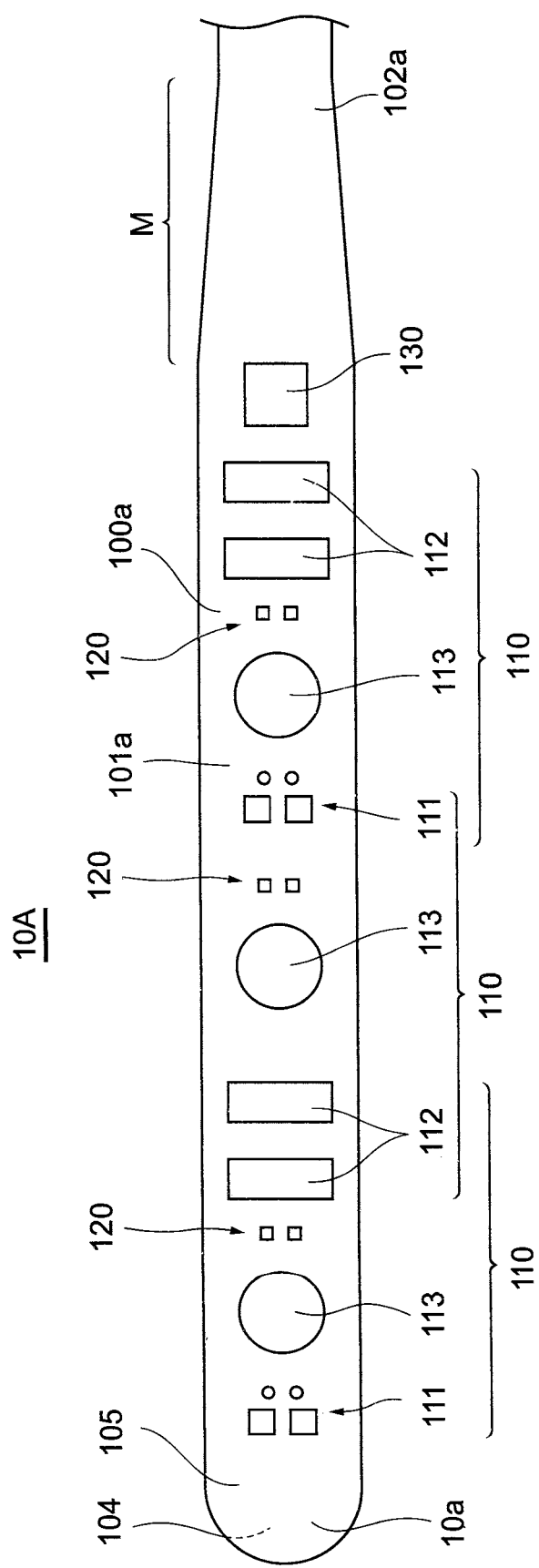
FIG. 14 is a plan view schematically showing a variation of the substrate shape.

FIG. 14 is a plan view schematically showing a variation of the substrate shape. As shown in FIG. 14, in the subdural sensor 10A, the width in the short-length direction of the wiring area 102a is smaller than the width in the short-length direction of the sensor area 101a. The sensor area 101a and the wiring area 102a are smoothy connected in a tapered manner. In the present variation, the wiring area 102a is not wound around, and the scalp is sutured around the planar wiring area 102a.

When the subdural sensor is pulled out from the suture point of the scalp after the sensor area of the subdural sensor has been placed in the subdural space for a predetermined period of time, a large force may be applied to the connection area between the sensor area and the wiring area.

As such, as shown in FIG. 14, by forming the connection area M between the sensor area 101a and the wiring area 102a in a tapered form, the substrate is prevented from being applied with a force at a specific point thereof when the subdural sensor 10A is pulled out, and the subdural sensor can be pulled out smoothly.

As another variation, the widths of the sensor area and the wiring area in the short-length direction may be aligned. In this case, the subdural sensor can also be pulled out smoothly.

Figure 15:
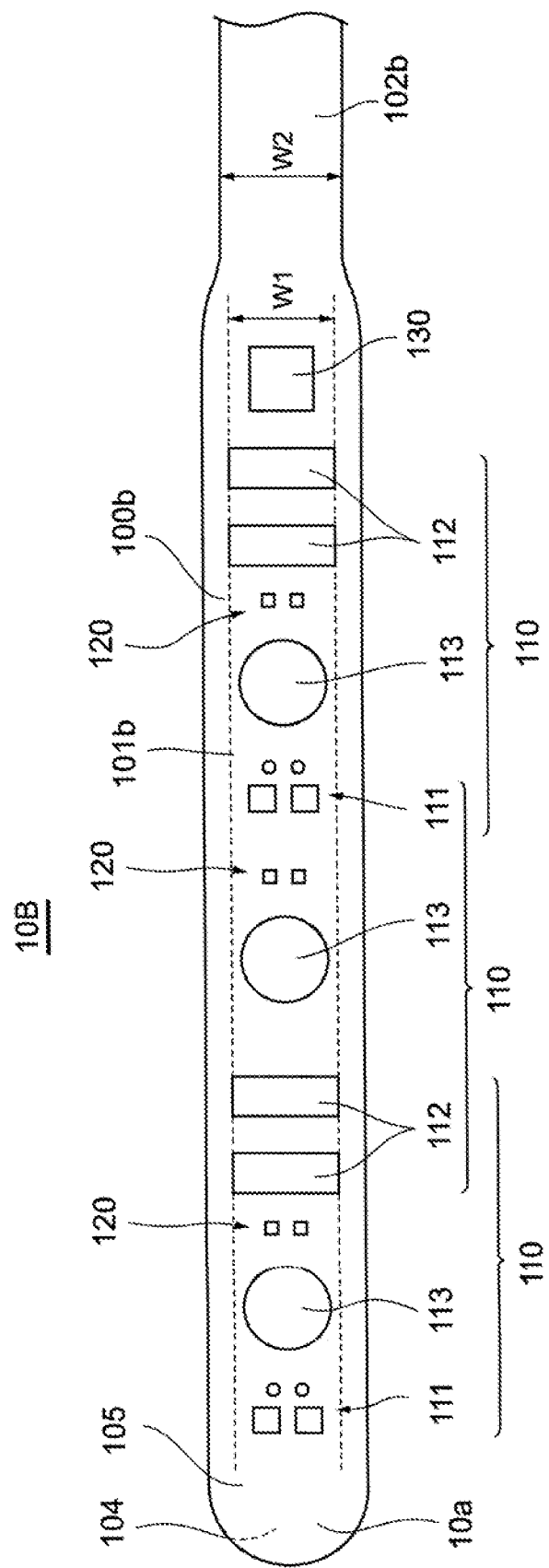
FIG. 15 is a plan view schematically showing another variation of the substrate shape.

FIG. 15 is a plan view schematically showing another variation of the substrate shape. FIG. 15 shows a plurality of sensor parts arranged in a line along the longitudinal direction of the substrate 100b in the sensor area 101b of the subdural sensor 10B. In contrast to the maximum width W1 of these sensor parts in the short-length direction of the substrate 100b, the width W2 in the short-length direction of the wiring area 102b is equal to or greater than the width W1. In the present variation, the wiring area 102b is not wound around, and the scalp is sutured around the planar wiring area 102b.

When the subdural sensor is pulled out from the suture point of the scalp after the sensor area of the subdural sensor has been placed in the subdural space for a predetermined period of time, a large force may be applied to the end of the sensor area which is wider than the wiring area.

As such, as shown in FIG. 15, by setting the width W2 of the wiring area 102b to be equal to or greater than the maximum width W1 of the sensor part, the deformation of the sensor area 101a may be confined to only the end area where no sensor parts are arranged, when the subdural sensor 10B is pulled out from the suture point of the scalp.

Figure 16:
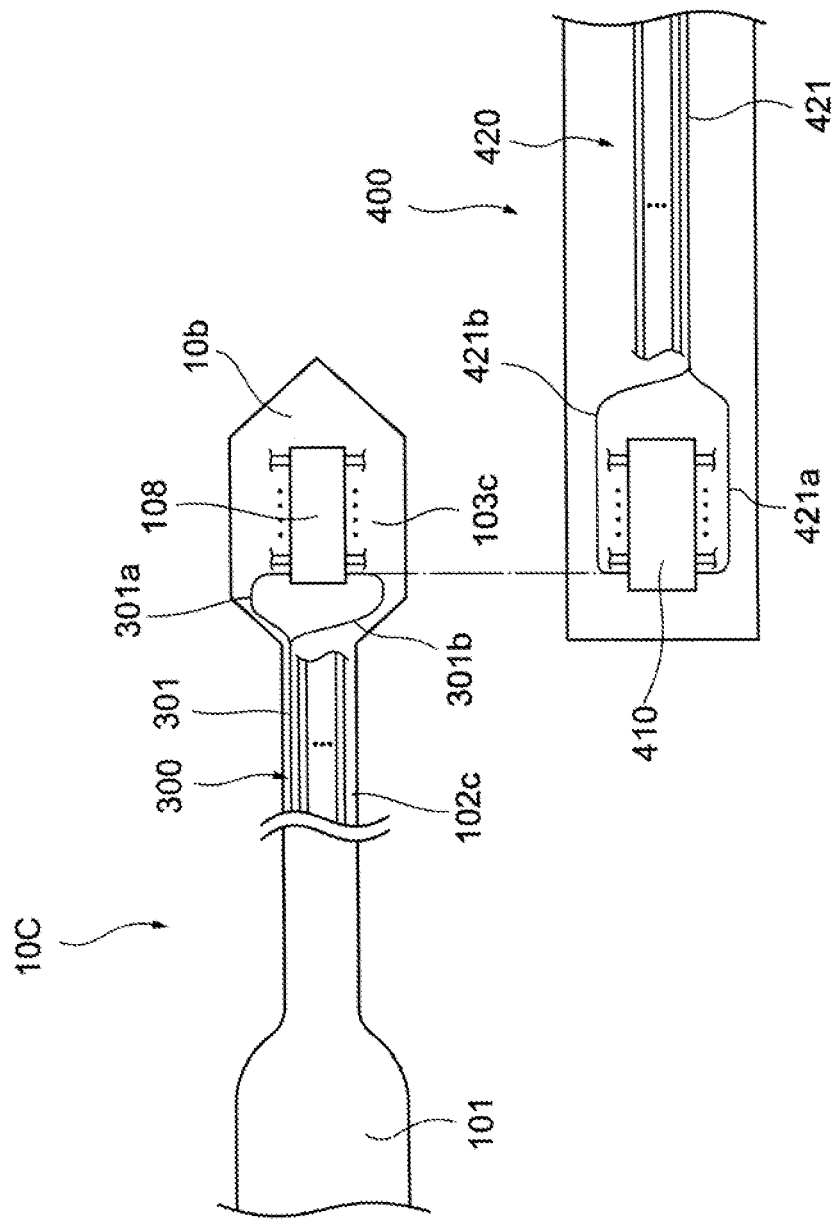
FIG. 16 is a plan view illustrating the wiring in a connector area.

FIG. 16 is a plan view illustrating the wiring in the connector area. As shown in FIG. 16, a signal line pattern 300 is formed in the wiring area of the subdural sensor 10C, which transmits the signals output from each sensor part arranged in the sensor area 101. Each signal line 301 included in the signal line pattern 300 is connected to a pin provided on the connector 108 mounted in the connector area 103c.

A cable 400 shown in FIG. 16 is composed of, for example, a flexible substrate, and intermediates between external devices, such as control devices, and the subdural sensor 10C. The cable 400 is mounted with an intermediary connector 410 (e.g., a female substrate-to-substrate connector), and a signal line pattern 420 corresponding to the signal line pattern 300 of the subdural sensor 10C is formed thereon. In using the subdural sensor 10C, the connector 108 is mated and electrically connected to the intermediary connector 410. The signals output from each sensor part are input to the external devices, such as control devices, via the signal line pattern 300, the connector 108, the intermediary connector 410, and the signal line pattern 420.

As shown in FIG. 16, in the present variation, each signal line 301 included in the signal line pattern 300 is divided into two branches in the connector area 103b, and the two branches are respectively connected to two different pins provided on the connector 108. On the other hand, each signal line 421 included in the signal line pattern 420 on the cable 400 side is also divided into two branches in the vicinity of the intermediary connector 410, and the two branches are respectively connected to two different pins provided on the intermediary connector 410. In other words, the signal output from each sensor part of the subdural sensor 10C is transmitted to the connector area 103c by a single signal line 301, passes through the two signal lines 301a, 301b branched off in the connector area 103c, is transmitted to the signal lines 421a, 421b on the cable 400 side via the connector 108 and the intermediary connector 410, and is then combined into a single signal line 421.

In this way, by transmitting a signal from the same origin through the signal lines 301a, 301b to the intermediary connector 410 via the two pins, a backup of the transmission route of the signals may be secured. In other words, even if a connection failure of one of the pins occurs between the connector 108 and the intermediary connector 410, the signal can still be reliably transmitted to the external device via the other pin.

The positions of the two pins connecting the branched signal lines 301a, 301b are not particularly limited, but it is preferable to select two pins respectively belonging to rows opposite to each other, as shown in FIG. 16. As a result, even if the connector 108 and the intermediary connector 410 are connected in a slightly slanted manner, the connection at at least one of the pins may still be secured.

Figure 17:
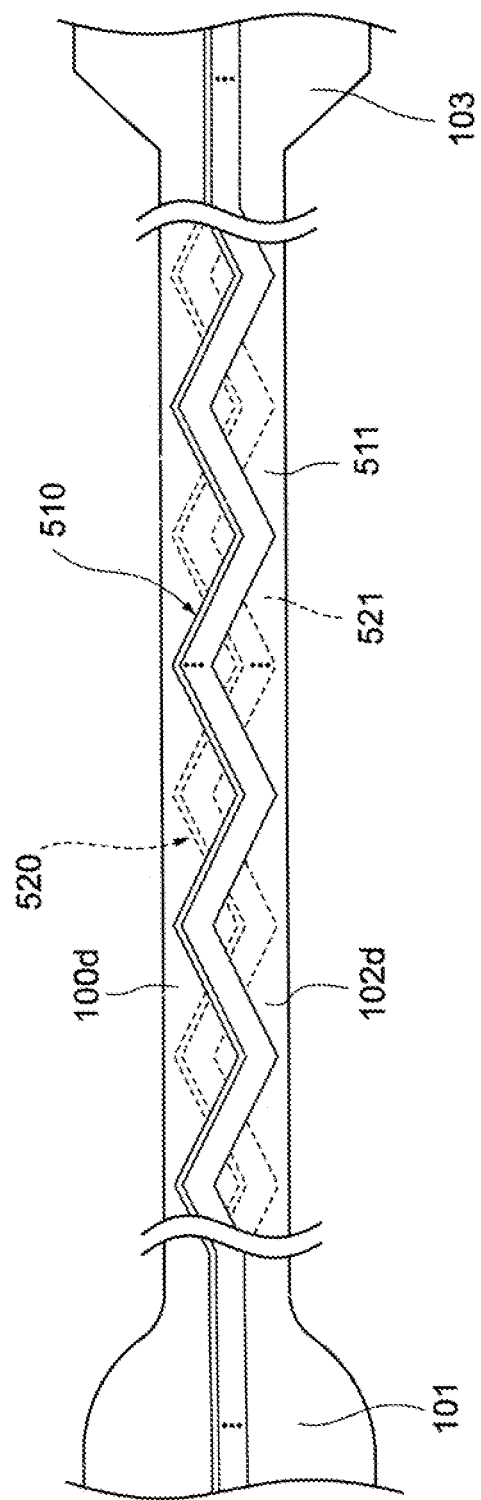
FIG. 17 is a plan view showing a variation of the wiring pattern in the wiring area.

FIG. 17 is a plan view showing a variation of the wiring pattern in the wiring area. In the present variation, a signal line pattern 510 of the wiring pattern is formed on one surface 511 of the substrate 100d and a power line pattern 520 is formed on the other surface 521 of the substrate 100d in the wiring area 102d. Then, the signal line pattern 510 and the power line pattern 520 are each formed in a wave shape where peaks and troughs appear in an alternating manner, and also formed such that peaks and troughs in the signal line pattern 510 are staggered with respect to peaks and troughs in the power line pattern 520.

As a specific example of the wave shape, it may be a triangular wave (zigzag) shape, as shown in FIG. 17, or a sine curve shape. Alternatively, the wave shape may have a shape where peaks and troughs of the triangular waves are curved, or a shape where arcs are connected. The distance between the peaks and troughs in each pattern may be adjusted appropriately according to the width in the short-length direction of the wiring area 102d and the number of signal and power lines (i.e., the width of each pattern).

In this way, by forming the signal line pattern 510 and the power line pattern 520 in an alternating manner so as to reduce the range in which these patterns run parallel, the effect of electromagnetic noise generated in the power line on the signals may be reduced.

The signal line pattern 510 and the power line pattern 520 may also be formed on different layers on the same surface instead of forming them on the respective surfaces of the substrate 100d. In short, each pattern should be formed so that, to the extent possible, the signal line pattern 510 and the power line pattern 520 do not run side-by-side.

Figure 18:
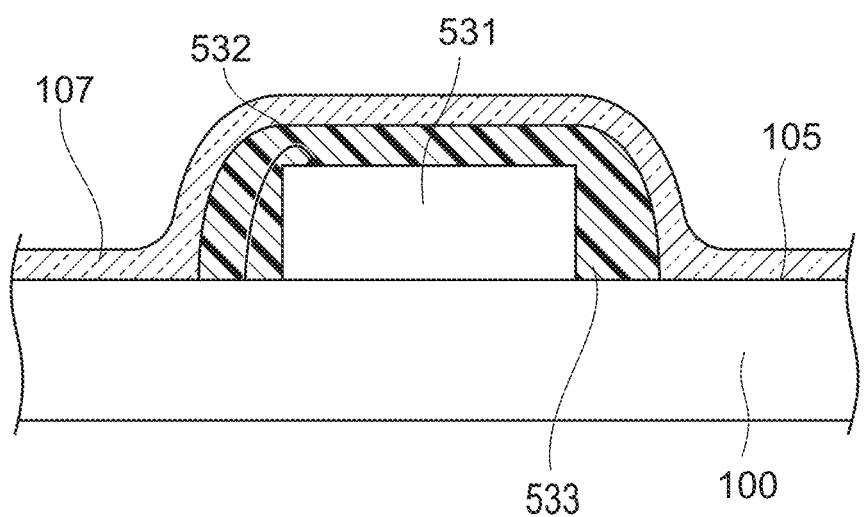
FIG. 18 is a partial cross-sectional view for describing an implementation of an element.

FIG. 18 is a partial cross-sectional view for describing an implementation of an element. When an element 531 contained in the sensor part is to be mounted on the substrate 100 by wire bonding, an insulation part 106 made of a flexible resin material, such as silicone, is preferably formed so as to cover the element 531 and wire 532 as a whole. As a result, the surrounding area of the element 531 can be reliably insulated, and the element 531 is brought into close contact with the substrate 100, further preventing the element 531 from falling off. In addition, by forming the film 107 on the upper layer, the flexibility of a mold 533 is regulated, and disconnection of the wire 532 is therefore prevented. As a variation, one element 531 may be bonded with two wires. In this case, the risk of disconnection may be reduced.

Figure 19:
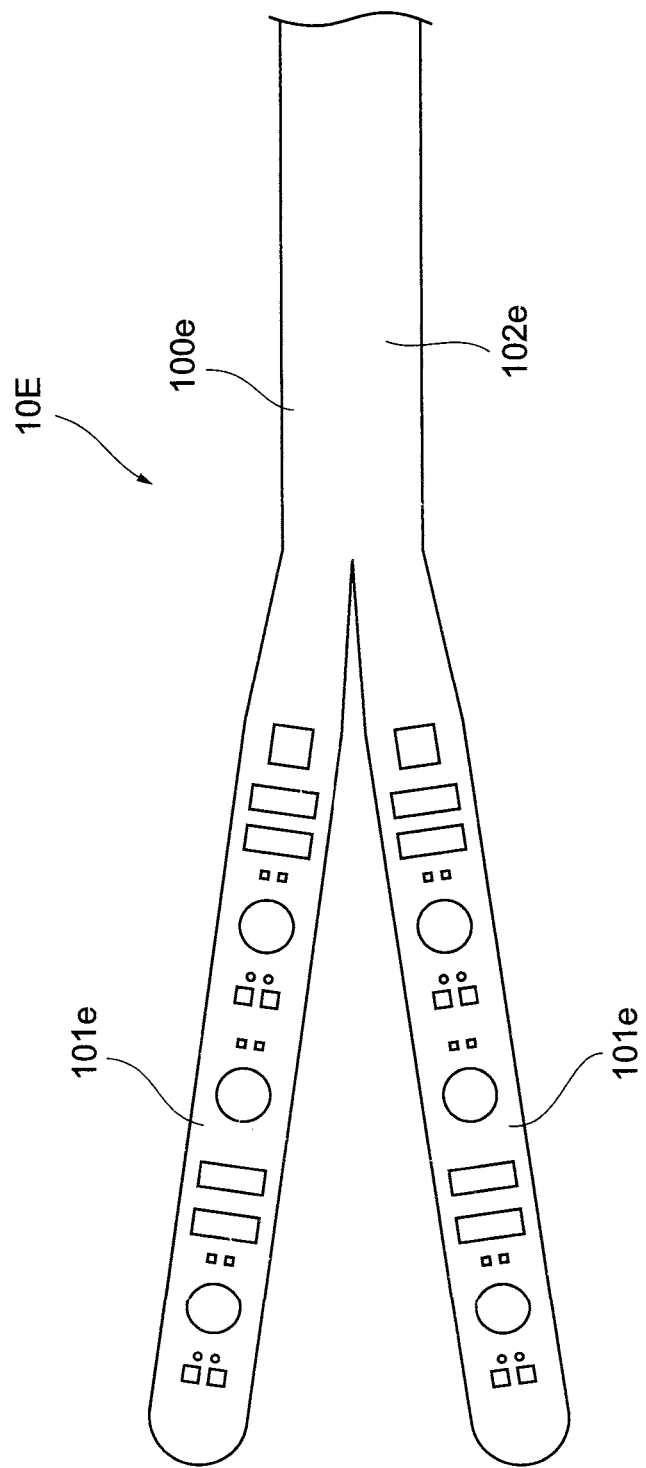
FIG. 19 is a plan view schematically showing a further variation of the subdural sensor.

FIG. 19 is a plan view schematically showing a further variation of the subdural sensor. The subdural sensor 10E shown in FIG. 19 is equipped with two sensor areas 101*e* and a wiring area 102*e* continuous with these sensor areas 101*e*. The configuration of the sensor parts provided in each sensor area 101*e* is the same as that shown in FIG. 1A. In this way, by branching the tip side of one substrate 100*e* to form a plurality of sensor areas, the measurable channel number of sensors can be increased and biological information about more regions can be acquired. In addition, by increasing the distance between the tips of the two sensor areas 101*e*, biological information on a wider region can be acquired.

Figure 20:
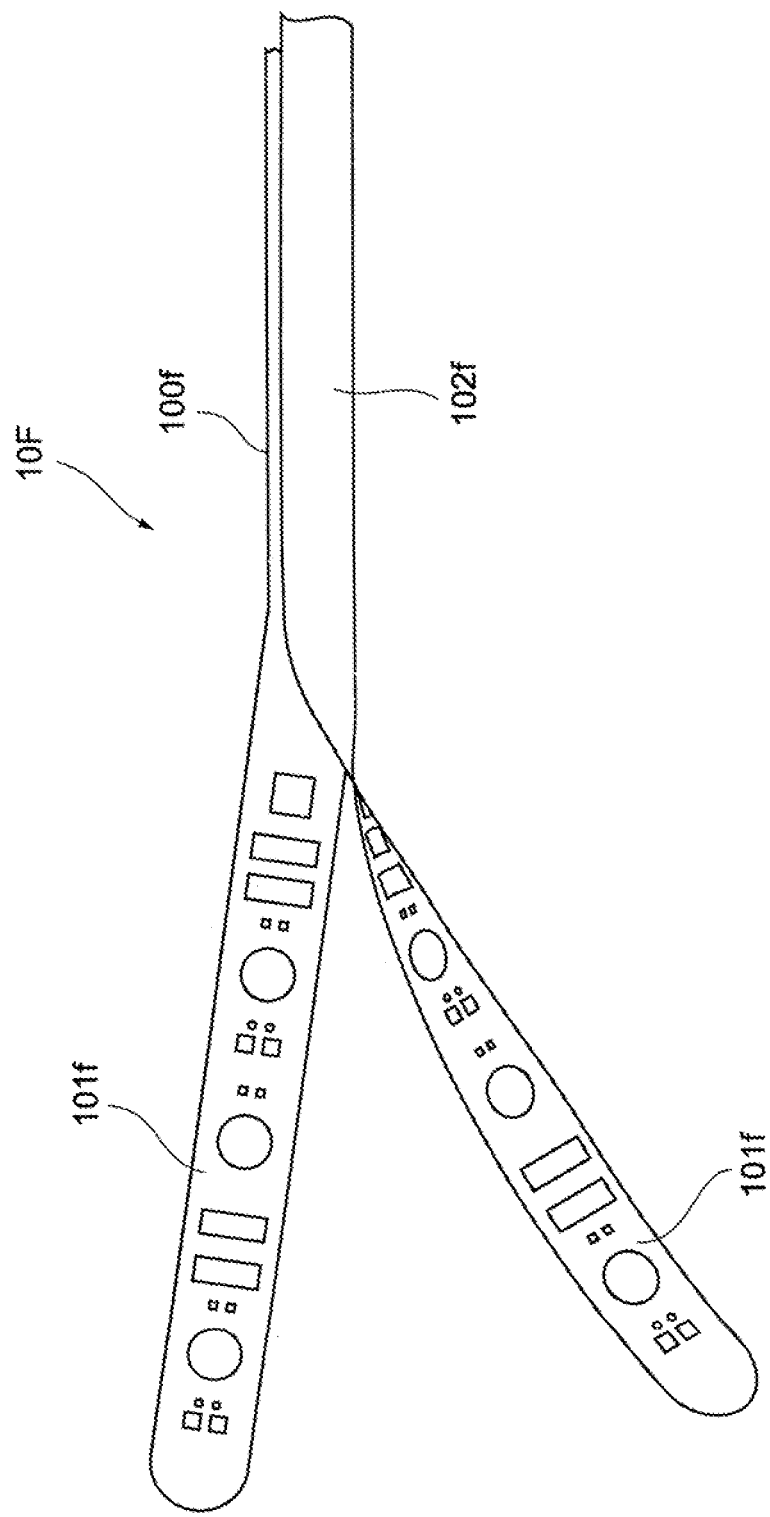
FIG. 20 is a plan view schematically showing a further variation of the subdural sensor.

FIG. 20 is a plan view schematically showing a further variation of the subdural sensor. In the subdural sensor 10F shown in FIG. 20, a notch is formed at the tip side of the strip-like substrate 100*f*, and the substrate 100*f* is separated along the longitudinal direction so as to form two sensor areas 101*f*. A portion of the wiring area 102*f* of the substrate 100*f* is folded along the longitudinal direction, so that when the two sensor areas 101*f* are arranged on the same surface, the distance between the tip parts of the two sensor areas 101*f* is naturally increased. The configuration of the sensor parts provided in each sensor area 101*f* is the same as that shown in FIG. 1A. According to the present variation, the processing of the shape of the substrate 100*f* may be simplified.

The present invention is not limited to the embodiments and variations described above, and may be carried out in various other forms within the scope that does not depart from the spirit of the present invention. For example, such various other forms may be formed by excluding some components from all of the components shown in the above-described embodiments and variations, or by appropriately combining the components shown in the above-described embodiments and variations.

Further advantages and modifications may be easily conceived of by those skilled in the art. Accordingly, from a wider standpoint, the present invention is not limited to the particular details and representative embodiments described herein. Accordingly, various modifications can be made without departing from the spirit or scope of the general idea of the invention defined by the appended claims and equivalents thereof.

What is claimed is:

1. A subdural sensor that is to be arranged in a subdural space and acquires biological information about the brain, comprising:
   a substrate formed of a flexible material; and
   at least one type of sensor part mounted on the substrate, wherein the substrate has an elongated shape as a whole, wherein the substrate includes:
      a sensor area in which the at least one type of sensor part is mounted and a wiring pattern connected to the at least one type of sensor part is formed;
      a wiring area contiguous with the sensor area on one end thereof, the wiring pattern extending in the wiring area; and
      a connector area contiguous with the other end of the wiring area, the connector area being an area on which a connector to be connected to the wiring pattern extending from the wiring area is mounted,
   wherein a tip part of the sensor area has a planar shape that curves convexly toward an outer periphery, and a side shape that curves toward a first surface, the first surface being on the side of a dura mater when the subdural sensor is inserted into the subdural space.

2. The subdural sensor according to claim 1, further comprising a cover that is formed of a soft material and covers the tip part of the sensor area.

3. The subdural sensor according to claim 1, wherein the at least one type of sensor part includes an intracranial pressure sensor mounted on an area in the vicinity of a tip part of the substrate.

4. The subdural sensor according to claim 3, further comprising a cover that is formed of a soft material, covers the tip part of the sensor area, and is arranged over a surrounding area of the intracranial pressure sensor.

5. The subdural sensor according to claim 1, wherein a width in the short-length direction of the wiring area is smaller than a width in the short-length direction of the sensor area, and a connection area between the sensor area and the wiring area is tapered.

6. The subdural sensor according to claim 1, wherein, in the sensor area, the at least one type of sensor part is arranged in a line along the longitudinal direction of the substrate, and
   wherein the width in the short-length direction of the wiring area is equal to or greater than the maximum width in the short-length direction of the substrate of the at least one type of sensor part arranged in the sensor area.

7. The subdural sensor according to claim 1, wherein the wiring pattern includes a signal line pattern and a power line pattern,
   wherein the signal line pattern is formed in a wave-shaped pattern on one surface of the wiring area, the wave-shaped pattern having peaks and troughs appearing in an alternating manner, and
   wherein the power line pattern is formed in a wave-shaped pattern on the other surface of the wiring area, the wave-shaped pattern having peaks and troughs that are staggered with respect to the peaks and the troughs of the signal line pattern.

8. The subdural sensor according to claim 1, wherein at least a portion of the wiring area is accommodated inside a tube formed of a flexible material.

9. The subdural sensor according to claim 1, wherein at least a portion of the wiring area is wound so as to form a cylindrical outer periphery shape as a whole.

10. The subdural sensor according to claim 9, wherein at least a portion of the wiring area is wound in a coiled form.

11. The subdural sensor according to claim 9, wherein at least a portion of the wiring area is divided into a plurality of strip-like areas along the longitudinal direction, and each of the plurality of strip-like areas is wound around one wire core.

12. The subdural sensor according to claim 11, wherein the wiring pattern includes a signal line pattern and a power line pattern,
   wherein at least a portion of the wiring area is divided, along the longitudinal direction, into a first strip-like area where the signal line pattern is formed and a second strip-like area where the power line pattern is formed, and wherein the first strip-like area and the second strip-like area are wound around the wire core in opposite directions to each other.

13. The subdural sensor according to claim 9, wherein an outer periphery surface of a wound portion of the wiring area is coated with a biocompatible material.

14. The subdural sensor according to claim 1, wherein the wiring pattern includes a signal line pattern that transmits a signal output from the at least one type of sensor part, and wherein each signal line included in the signal line pattern divides into two branches in the connector area and the two branches are respectively connected to two different pins provided on the connector.

15. The subdural sensor according to claim 1, wherein the at least one type of sensor part includes a blood flow measurement part that includes a light-emitting element capable of emitting near-infrared light, a light-receiving element capable of receiving near-infrared light, and a light reflection part arranged between the light-emitting element and the light-receiving element, and the light reflection part has a shape in which at least a circumferential part bulges toward an inner periphery.

16. The subdural sensor according to claim 15, wherein the light reflection part also serves as an electrode for electrocorticogram measurement.

17. The subdural sensor according to claim 15, wherein the at least one type of sensor part includes a temperature measurement element arranged inside the light reflection part.

18. The subdural sensor according to claim 16, wherein the at least one type of sensor part includes a temperature measurement element arranged inside the light reflection part.

* * * * *